US00PP36462P3

(12) United States Plant Patent
Schoone

(10) Patent No.: US PP36,462 P3
(45) Date of Patent: Feb. 18, 2025

(54) ***PHALAENOPSIS* PLANT NAMED 'Sirocco Waves'**

(50) Latin Name: *Phalaenopsis hybrida*
Varietal Denomination: Sirocco Waves

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/625,176

(22) Filed: Apr. 2, 2024

(65) Prior Publication Data

US 2024/0334855 P1 Oct. 3, 2024

Related U.S. Application Data

(60) Provisional application No. 63/456,505, filed on Apr. 2, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./263.1, 311
See application file for complete search history.

(56) References Cited

U.S. PATENT DOCUMENTS

PP29,177 P3 * 4/2018 Schoone ..... A01H 6/62
Plt./311

* cited by examiner

*Primary Examiner* — Karen M Redden
(74) *Attorney, Agent, or Firm* — C. Anne Whealy

(57) ABSTRACT

A new and distinct cultivar of *Phalaenopsis* plant named 'Sirocco Waves', characterized by its upright plant habit; moderately vigorous to vigorous growth habit; strong flowering stems; strong leaves; freely flowering habit with typically three inflorescences developing per plant, each inflorescence with numerous flowers; flowers with bright reddish purple-colored petals with light purple-colored dots; and good postproduction longevity.

2 Drawing Sheets

Figure 1:
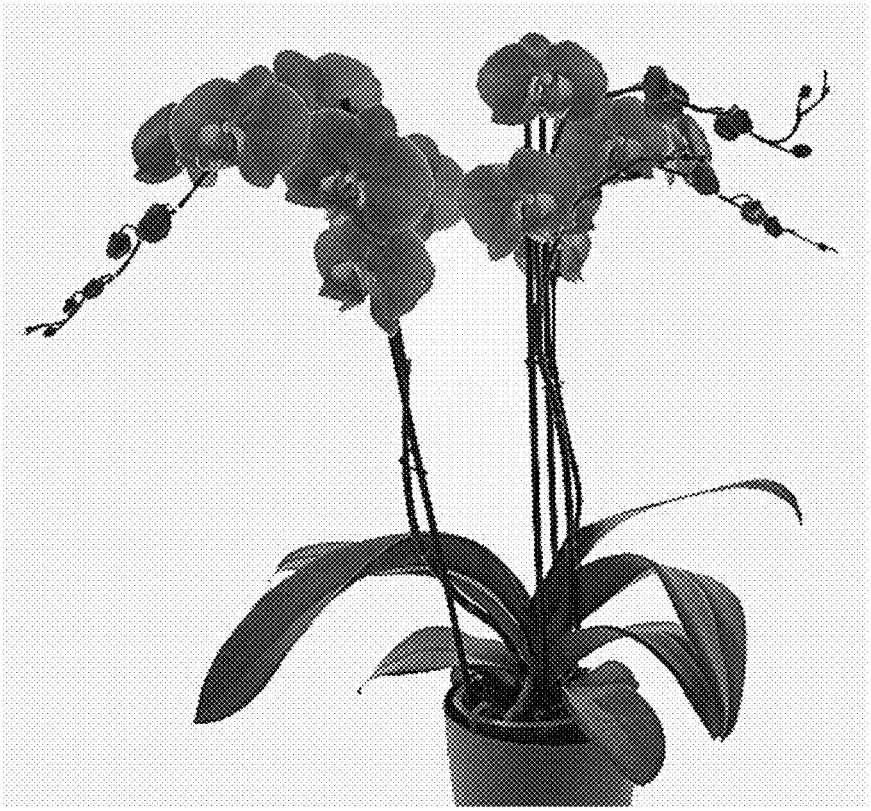

Botanical designation: *Phalaenopsis hybrida.*
Cultivar denomination: 'SIROCCO WAVES'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B. V. of Heemskerk, The Netherlands on Feb. 27, 2023, application number 2023/0527. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Sirocco Waves'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in February 2013 in Nantou, Taiwan of *Phalaenopsis hybrida* 'Sogo Davis', not patented, as the female, or seed, parent with *Phalaenopsis hybrida* 'Luchia Pink' X 'Sogo Pinkama', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October 2019.

Asexual reproduction of the new *Phalaenopsis* plant by in vitro meristem propagation in a controlled environment in Assendelft, The Netherlands since October 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sirocco Waves'. These characteristics in combination distinguish 'Sirocco Waves' as a new and distinct *Phalaenopsis* plant:

1. Upright plant habit.
2. Moderately vigorous to vigorous growth habit.
3. Strong flowering stems.
4. Strong leaves.
5. Freely flowering habit with typically three inflorescences developing per plant, each inflorescence with numerous flowers.
6. Flowers with bright reddish purple-colored petals with light purple-colored dots.
7. Good postproduction longevity.

Plants of the new *Phalaenopsis* can be compared to plants of the female parent, 'Sogo Davis'. Plants of the new *Phalaenopsis* differ primarily from plants of 'Sogo Davis' in labellum color as the labellum of plants of the new *Phalaenopsis* is mostly white with reddish purple and yellow in color whereas the labellum of plants of 'Sogo Davis' is dark purplish red in color. In addition, the petals of plants of the new *Phalaenopsis* are not striped or netted whereas the petals of plants of 'Sogo Davis' are striped and netted.

Plants of the new *Phalaenopsis* can be compared to plants of the male parent, 'Luchia Pink' X 'Sogo Pinkama'. Plants of the new *Phalaenopsis* differ primarily from plants of 'Luchia Pink' X 'Sogo Pinkama' in labellum color as the labellum of plants of the new *Phalaenopsis* is mostly white with reddish purple and yellow in color whereas the labellum of plants of 'Luchia Pink' X 'Sogo Pinkama' is dark purplish red in color. In addition, the cirrhose tips of plants of the new *Phalaenopsis* are white in color whereas the cirrhose tips of plants of 'Luchia Pink' X 'Sogo Pinkama' are dark purplish red in color.

Plants of the new *Phalaenopsis* can be compared to plants of *Phalaenopsis hybrida* 'Purple Dust', disclosed in U.S. Plant Pat. No. 29,177. In side-by-side comparisons, plants of the new *Phalaenopsis* differ primarily from plants of 'Purple Dust' in the following characteristics:

1. Plants of the new *Phalaenopsis* are taller than plants of 'Purple Dust'.
2. Leaves of plants of the new *Phalaenopsis* are more upright than and not as drooping as leaves of plants of 'Purple Dust'.
3. Flowers of plants of the new *Phalaenopsis* are not as broad as flowers of plants of 'Purple Dust'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Sirocco Waves' grown in a container.

Figure 2:
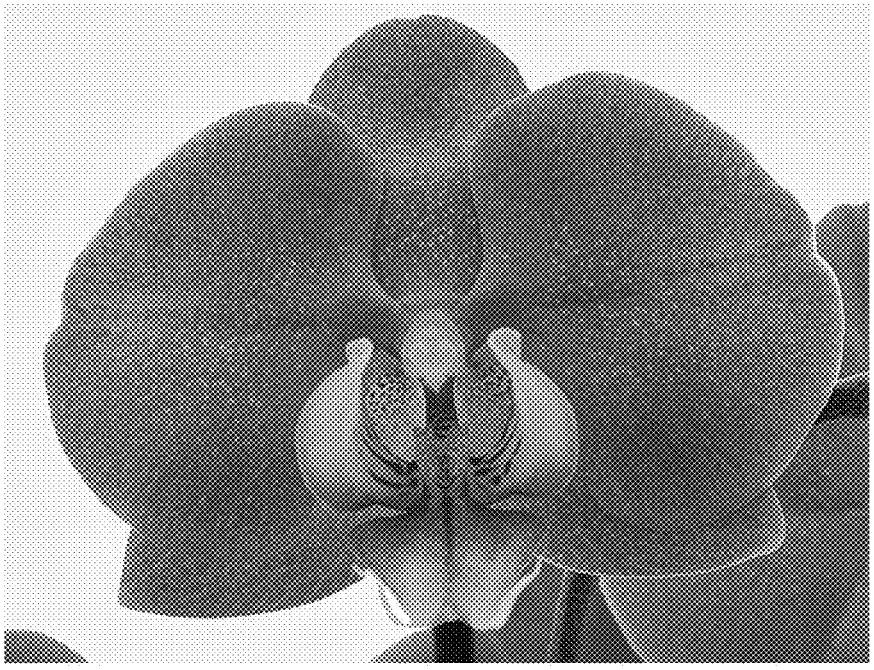

The photograph on the second sheet (FIG. 2) is a close-up view of a typical flower of 'Sirocco Waves'.

DETAILED BOTANICAL DESCRIPTION

The aforementioned photographs and following observations and measurements describe plants grown during the late winter and early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Sirocco Waves'.

Parentage:

*Female, or seed, parent.*—*Phalaenopsis hybrida* 'Sogo Davis', not patented.

*Male, or pollen, parent.*—*Phalaenopsis hybrida* 'Luchia Pink' X 'Sogo Pinkama', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically three inflorescences developing per plant, each inflorescence with numerous flowers; monopodial; moderately vigorous to vigorous growth habit and moderate growth rate.

*Plant height, substrate level to top of foliar plane.*—About 15.1 cm.

*Plant height, substrate level to top of floral plane.*—About 46 cm.

*Plant diameter or spread.*—About 38.1 cm.

Leaf description:

*Arrangement and quantity.*—Distichous, simple; sessile; about four fully-developed leaves per plant.

*Length.*—About 25.4 cm.

*Width.*—About 7.2 cm.

*Aspect.*—Semi-erect and eventually outwardly arching.

*Shape.*—Narrowly oblong to oblanceolate; slightly carinate and moderately reflexed.

*Apex.*—Unequal acute.

*Base.*—Sheathing. Sheath length: About 2.1 cm. Sheath width: About 1.7 cm. Sheath color: Close to 146C with margins, close to N77A.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Darker than a blend of NN137A and 146A. Developing leaves, lower surface: Close to 146A strongly tinged with close to N186C. Fully expanded leaves, upper surface: Close to NN137C; venation, darker than 147A. Fully expanded leaves, lower surface: Close to 146B; margins and venation strongly tinged with close to N186C.

Inflorescence description:

*Appearance and flowering habit.*—Showy zygomorphic flowers arranged on axillary simple or branched racemes; typically three inflorescences develop per plant; each inflorescence with about 18 flowers; flowers face outwardly on outwardly arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length* (*lowermost flower to inflorescence apex*).—About 32.5 cm.

*Inflorescence width.*—About 15.4 cm.

*Flower buds.*—Height: About 1.8 cm. Diameter: About 1.3 cm by 1.6 cm. Shape: Broadly ovate. Color: Close to 177B; sepal margins, close to N77B.

*Flower size.*—About 6.9 cm (vertical) by 8.5 cm (horizontal).

*Flower depth.*—About 2.9 cm.

*Petals, quantity and arrangement.*—Three, two lateral petals and one center petal transformed into a labellum.

*Lateral petals.*—Length: About 3.9 cm. Width: About 5.1 cm. Shape: Roughly lunate. Apex: Retuse, broad and shallow. Margin: Entire; not undulate. Texture and luster, upper and lower surfaces: Smooth, glabrous; velvety; matte. Color: When opening, upper surface: Close to N78A with fine dots, close to 76B; proximally, close to N78B and N80B and at the base, close to N78A. When opening, lower surface: Close to N80B; towards the center, close to 75D. Fully opened, upper surface: Close to a blend of N78B and NN78B with fine dots, close to 76B; towards the apex and base, tinged with close to N78C; at the base, close to NN78B. Fully opened, lower surface: Close to N80B; towards the center, close to N80D.

*Labella.*—Appearance: Three-parted with two lateral lobes and a central lobe. Length, lateral lobes: About 2.1 cm. Width, lateral lobes: About 1.5 cm. Length, central lobe: About 2.2 cm. Width, central lobe: About 0.8 cm to 1.9 cm. Length, cirrhose tips: About 1.1 cm. Shape, lateral lobes: Obovate. Shape, central lobe: Deltoid with a slightly elongate apex. Apex, lateral lobes: Obtuse. Apex, central lobe: Cleft with two upwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 5 mm in width and about 6.5 mm in height. Color: When opening, upper surface: Lateral lobes: Close to 76D; towards the center and base, close to 158D; lower margin, close to 4C; edges, close to 174B; at the base, stripes, close to 71A. Central lobe: Close to 11D; towards the base, close to N78B and N77B and at the base, close to a blend of 76D and NN155D and N78D with stripes, close to N79C; cirrhose tips, close to 155C. When opening, lower surface: Lateral lobes: Close to 76C to 76D; towards the center, close to a blend of 4D and 155C; lower margin, tinged with close to 4B; distally, fine dots, close to 77B. Central lobe: Close to 76D with marbling and fine dots, close to N75A; towards the center and margins, tinged with close to 177D; base, close to 70A and a blend of 76C and 156D; cirrhose tips, close to 155C. Fully opened, upper surface: Lateral lobes: Close to 76D; lower margin, close to 20B; edges, close to 168B; at the base, stripes, close to 71A. Central lobe: Close to N75B; towards the margins and apex, close to NN155D; towards the base, close to N78B with margins, strongly tinged with close to 174B; at the base, close to N78B and N78C with stripes, close to N79C; cirrhose tips, close to NN155D. Fully opened, lower surface: Lateral lobes: Close to NN155C with dense fine dots, close to 172B; towards the apex, strongly tinged and dotted with close to N78B; lower margins, tinged with close to 22B; at the base, close to N78A. Central lobe: Close to 77C; towards the apex and base, close to N78B; margins at the widest part, close to 173B; at the base, close to 70A and a blend of 76C and 156D; cirrhose tips, close to N155A. Callosities: When developing, inner and outer surfaces: Close to 12D with fine dots, close to 178A; margins, close to 12B. Fully developed, inner and outer surfaces: Close to 12D with fine dots, close to 178A; margins, close to 12B.

*Sepals.*—Quantity and arrangement: Three, one upper dorsal sepal and two lower lateral sepals. Length, dorsal sepal: About 3.9 cm. Width, dorsal sepal: About 2.7 cm. Length, lateral sepals: About 3.9 cm. Width, lateral sepals: About 2.5 cm. Shape, dorsal sepal: Broadly elliptic. Shape, lateral sepals: Ovate. Apex, dorsal sepal: Retuse, minute. Apex, lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to N78A with fine dots, close to 76B; towards the apex, close to N78B and N80B. When opening, lower surface: Close to N78A and N78B; towards the center, strongly tinged with close to 182B. Fully opened, upper surface: Close to NN78A with fine dots, close to 76B; towards the apex, close to N78B. Fully opened, lower surface: Close to N78B; towards the center, close to 70B. Color, lateral sepals: When opening, upper surface: Close to N78B with fine dots, close to 76B; towards the base, strongly tinged with close to 195C with dots, close to N79C. When opening, lower surface: Close to 70A; towards the center, tinged with close to 182B; main vein, close to 178A. Fully opened, upper surface: Close to N78B with fine dots, close to 76B; towards the base, close to 77C with dots, close to 72A. Fully opened, lower surface: Close to N78B; towards the center, close to 70B.

*Peduncles.*—Length: About 56.6 cm. Diameter: About 6 mm. Strength: Strong. Aspect: Upright to outwardly arching. Texture and luster: Smooth, glabrous; matte. Color: Close to N200A marbled and densely covered with fine dots, close to 147D.

*Pedicels.*—Length: About 3.8 cm. Diameter: About 3 mm. Strength: Moderately strong. Aspect: About 50° From peduncle axis. Texture and luster: Smooth, glabrous; matte. Color: Close to a blend of 195A and 197C; proximally, close to 197A; distally, flushed with close to 76C.

*Reproductive organs.*—Androecium: Column length: About 9 mm. Column width: About 6 mm. Column color: Close to N78C; distally, close to 76A. Pollinia quantity: Two. Pollinia diameter (per two pollinia): About 3 mm. Pollinia color: Close to 24A. Gynoecium: Stigma length: About 4 mm. Stigma width: About 4 mm. Stigma shape: Reniform. Stigma color: Close to N155A. Ovary length: About 1.1 cm. Ovary diameter: About 1 mm. Ovary color: Close to 150C. Seeds and fruits: To date, seed and fruit development have not been observed on plants of the new *Phalaenopsis.*

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Sirocco Waves' as herein illustrated and described.

* * * * *